United States Patent
Larsen et al.

(10) Patent No.: US 9,358,309 B2
(45) Date of Patent: *Jun. 7, 2016

(54) RADIOIMUNOCONJUGATES AND USES THEREOF

(71) Applicant: Nordic Nanovector AS, Oslo (NO)

(72) Inventors: Roy H. Larsen, Oslo (NO); Jostein Dahle, Haslum (NO); Øyvind S. Bruland, Oslo (NO)

(73) Assignee: Nordic Nanovector AS, Oslo (NO)

( * ) Notice: Subject to any disclaimer, the term of this patent is extended or adjusted under 35 U.S.C. 154(b) by 136 days.

This patent is subject to a terminal disclaimer.

(21) Appl. No.: 14/100,756

(22) Filed: Dec. 9, 2013

(65) Prior Publication Data

US 2014/0147384 A1 May 29, 2014

Related U.S. Application Data

(62) Division of application No. 13/522,678, filed as application No. PCT/EP2011/051231 on Jan. 28, 2011, now Pat. No. 8,628,749.

(60) Provisional application No. 61/299,524, filed on Jan. 29, 2010.

(30) Foreign Application Priority Data

Jan. 29, 2010 (NO) .................................. 20100143

(51) Int. Cl.
*A61K 51/10* (2006.01)
*C07K 16/28* (2006.01)

(52) U.S. Cl.
CPC ......... *A61K 51/1069* (2013.01); *A61K 51/1027* (2013.01); *A61K 51/1093* (2013.01); *C07K 16/2896* (2013.01)

(58) Field of Classification Search
CPC ........... A61K 51/1027; A61K 51/1069; A61K 51/1093; C07K 16/2896; C07K 16/2887
See application file for complete search history.

(56) References Cited

U.S. PATENT DOCUMENTS

| | | | | |
|---|---|---|---|---|
| 6,090,365 A * | 7/2000 | Kaminski | .......... | A61K 51/1069 424/1.49 |
| 2002/0009444 A1 * | 1/2002 | Grillo-Lopez | ... | A61K 39/39541 424/142.1 |
| 2004/0241158 A1 * | 12/2004 | McBride | .......... | A61K 47/48723 424/130.1 |
| 2005/0191239 A1 | 9/2005 | Griffiths et al. | | |

FOREIGN PATENT DOCUMENTS

| | | |
|---|---|---|
| JP | 2009-502171 A | 1/2009 |
| WO | WO 2007/014278 A2 | 2/2007 |
| WO | WO 2009/019312 | 2/2009 |

OTHER PUBLICATIONS

Tol et al., N Engl J Med. 5;360(6):563-72, Feb. 2009.*
Zuckier et al., Cancer Research 58: 3905-3908, 1998.*
Jubala et al., Vet Pathol 42: 468-476, 2005.*
Bienert et al., "Radioimmunotherapy using $^{131}$I-rituximab in patients with advanced stage B-cell non-Hodgkin's lymphoma: initial experience," *European Journal of Nuclear Medicine and Molecular Imaging*, vol. 32, No. 10; 1225-1233; (2005).
Buchsbaum et al., "Therapy with Unlabeled and $^{131}$I-labeled Pan-B-Cell Monoclonal Antibodies in Nude Mice Bearing Raji Burkitt's Lymphoma Xenografts," *Cancer Research*, 52; 6476-6481; (1992).
Colman, Effects of amino acid sequence changes on antibody-antigen interactions, *Res Immunol.*, 145(1); 33-36; (1994).
Dufner et al., "Harnessing phage and ribosome display for antibody optimisation," *Trends in Biotechnology*, vol. 24, No. 11; 523-529; (2006).
Henriksen et al., "Bi-labelled antibody and Bi-labelled streptavidin. Comparison of targeting efficacy of a lymphoma cell line in vitro," *Journal of Labelled Compounds and Radiopharmaceuticals*, vol. 34, No. 12; 1039-1046; (1997).
Kaminski et al., "Imaging, Dosimetry, and Radioimmunotherapy With Iodine [131]I-Labeled Anti-CD37 Antibody in B-Cell Lymphoma," *Journal of Clinical Oncology*, vol. 10, No. 11; 1696-1711; (1992).
Koppe et al., "Antibody-guided radiation therapy of cancer," *Cancer and Metastasis Reviews* 24; 539-567; (2005).
Pandit-Taskar et al., "New Strategies in Radioimmunotherapy for Lymphoma," *Current Oncology Reports* 5; 364-371; (2003).
Press et al., "Treatment of Refractory Non-Hodgkin's Lymphoma With Radiolabeled MB-1 (Anti-CD37) Antibody," *Journal of Clinical Oncology*, vol. 7, No. 8; 1027-1038; (1989).
Press et al., "Radolabeled-Antibody Therapy of B-Cell Lymphoma With Autologous Bone Marrow Support," *The New England Journal of Medicine*, vol. 329, No. 17; 1219-1224; (1993).
Riemer et al., "Matching of trastuzumab (Herceptin®) epitope mimics onto the surface of Her-2/neu—a new method of epitope definition," *Molecular Immunology* 42; 1121-1124; (2005).
Smeland et al., "Characterization of Two Murine Monoclonal Antibodies Reactive with Human B Cells: Their Use in a High-Yield, High-Purity Method for Isolation of B Cells and Utilization of Such Cells in an Assay for B-Cell Stimulating Factor," *Scand. J. Immunol.* 21; 205-214; (1985).
Stancovski et al., "Mechanistic aspects of the opposing effects of monoclonal antibodies to the ERBB2 receptor on tumor growth," *Proc. Natl. Acad. Sci.* 88; 8691-8695; (1991).
Wu et al., "Humanization of a Murine Monoclonal Antibody by Simultaneous Optimization of Framework and CDR Residues," *J. Mol. Biol.* 294; 151-162; (1999).
Fani, M. et al., "Lu-labeled-VG76e monoclonal antibody in tumor angiogenesis: A comparative study using DOTA and DTPA chelating systems" Radiochim. Acta, 2007, pp. 351-357, vol. 95.
Proceedings of the 46th Isotope/Radiation Research Conference (in Japanese), Jun. 20, 2009, pp. 82, 2a-III-10.
Program and Proceedings of the 13th Annual Meeting of Japanese Society of Cancer Immunology (in Japanese), May 20, 2009, p. 42.

* cited by examiner

*Primary Examiner* — Phuong Huynh

(74) *Attorney, Agent, or Firm* — Knobbe, Martens, Olson & Bear, LLP

(57) ABSTRACT

The present invention relates to a radioimmunoconjugate that binds human CD37. Pharmaceutical compositions and uses thereof for the treatment of cancer and in particular B cell malignancies are aspects of the present invention.

11 Claims, 8 Drawing Sheets

RADIOIMUNOCONJUGATES AND USES THEREOF

CROSS-REFERENCE TO RELATED APPLICATIONS

This application is a divisional of and claims the benefit of and priority to U.S. patent application Ser. No. 13/522678, filed on Aug. 14, 2012, which is now U.S. Pat. No. 8,628,749, which is a U.S. National Phase application of PCT International Application Number PCT/EP2011/051231, filed on Jan. 28, 2011, designating the United States of America and published in the English language, which is an International Application of and claims the benefit of priority to United States Provisional Patent Provisional Application No. 61/299,524, filed on Jan. 29, 2010, and Norwegian Patent Application No. 20100143. The disclosures of the above-referenced applications are hereby expressly incorporated by reference in their entireties.

REFERENCE TO SEQUENCE LISTING

The present application is being filed along with a sequence listing in electronic format. The sequence listing is provided as a file entitled SequenceListing-PLOUG110-001D1, created Dec. 6, 2013 which is 4 KB in size. The information in the electronic format of the sequence listing is incorporated herein by reference in its entirety.

FIELD OF THE INVENTION

The present invention relates to radioimmunotherapy of hematologic cancer with a radiolabeled monoclonal antibody with an unexpectedly high cytotoxicity.

BACKGROUND OF THE INVENTION

Therapy with radiolabeled antibodies has been introduced against non-Hodgkin lymphoma (NHL) and is an approved method today. Two products are on the market, Zevalin™ and Bexxar™, and both targets the CD20 antigen (Jacene et al., 2007).

Also the immunotherapeutic agent rituximab (Rituxan™/Mabthera™) targets the CD20 antigen. One problem with treatment against the same target is the possibility of immunophenotypic drift during the disease course (Ngo et al., 2009) which could cause diminished effects of CD20 therapy when repeated over time as in rituximab therapy or if CD20-based radioimmunotherapy (RIT) is administered following prolonged rituximab therapy.

A large number of patients receiving CD20 directed therapy will eventually experience relapse (Buchegger et al., 2006; Gordon et al 2004). Thus, there is a significant need for RIT that targets another antigen than the CD20 in NHL patients.

In the early development of RIT, the two antigens CD37 and CD20 were evaluated as targets (Press et al., 2001). It was concluded that the CD20 targeting RIT was more appropriate and therefore the development of CD37 directed RIT was abandoned. Thus, it is known in the art that monoclonal antibodies are suitable for use in RIT against lymphoma, but that radioimmunoconjugate (RIC) targeting CD20 is superior to RIC targeting CD37 (Press et al., 2001).

In recent years CD37 has attracted some new interest (Heider et al., 2009; Grosmaire, 2007), mainly as target for immunotherapy using chimeric or humanized antibody constructs. These works teaches away from using conventional murine IgG monoclonal antibodies, since murine antibodies may induce human anti-mouse antibody (HAMA) production in patients, which can cause discomfort and reduced efficacy of immunotherapies.

For RIT, conventional murine monoclonal antibodies are still considered interesting, since in general the protein doses used are lower and the treatment need not being repeated to the same extent as with immunotherapy. Also the clearance of murine IgG is generally slightly faster than humanized or chimeric versions of the same IgG, which may be more appropriate in terms of whole body radiation exposure from RIT, at least in some settings. It should be noted that both Bexxar and Zevalin are based on murine antibodies.

The present invention provides the anti-CD37 murine antibody HH1 as carrier for radioisotope. The original hybridoma clone that produces the murine anti-CD37 antibody HH1 was developed in the 1980's (Smeland et al., 1985) and the HH1 antibody has been in sale for in vitro use in immunohistochemistry for several years.

HH1 has not previously been evaluated for radioimmunotherapy in terms of biodistribution and cellular cytotoxicity. The current work was therefore undertaken to evaluate the suitability of HH1 in radioimmunotherapy. In contrast to the previous clinical and preclinical work with anti-CD37 RIC, which used $^{131}$I directly radiolabeled to the tyrosine residues using the chloramineT/Iodogen methods, the HH1 was radiolabeled via a chelator using a metallic radionuclide instead of a halogen.

Using a metallic radionuclide labeled via a chelator-linker could be advantageous since the use of $^{131}$I-labeled antibodies is associated with the exposure of the thyroid to various amounts of iodine released from the RIC's.

In a previous study to evaluate whether HH1 was suitable for producing a radioimmunoconjugate CHX-A-DTPA was conjugated to HH1 and the conjugate labeled with $^{205,206}$Bi for in vitro modeling purposes (Henriksen et al., 1997).

The uptake in the cell line Raji was compared for bismuth conjugated to HH1 or streptavidin. In the latter case cells had been presaturated with biotinylated-HH1.

It was found that the number of chelators required to ensure functional RIC when labeled with $^{212}$Bi or $^{213}$Bi was a limiting factor. It was therefore suggested to use biotinylated HH1 instead of a HH1 based RIC. Once bound to the cells, the biotinylated HH1 could then be targeted with radiolabeled streptavidin.

Thus, the work suggests that HH1 labeled with an alpha-particle-emitting radionuclide was less useful due to insufficient specific activity at the chelator concentrations deemed tolerable for the HH1 to retain sufficient binding ability.

It was also indicated in the paper that a beta-emitter would be even less suitable for constructing a functional RIC compared with an alpha-emitter (Henriksen et al, 1997) as the authors stated that targeted radiotherapy with beta-emitter should be inferior in disseminated disease because cross-fire is essential for obtaining sufficient effect.

Thus, the above cited work teaches away from using a directly chelated HH1 in radioimmunotherapy and also away from using HH1 in a beta-emitter based RIC.

SUMMARY OF THE INVENTION

The present invention relates to a radioimmunoconjugate that binds human CD37 comprising murine monoclonal antibody HH1, a linker, and a radionuclide selected from the group consisting of $^{211}$At, $^{213}$Bi, $^{212}$Bi, $^{212}$Pb, $^{225}$Ac, $^{227}$Th, $^{90}$Y, $^{186}$Re, $^{188}$Re, $^{199}$Au, $^{194}$Ir, $^{166}$Ho, $^{159}$Gd, $^{153}$Sm, $^{149}$Pm, $^{142}$Pr, $^{111}$Ag, $^{109}$Pd, $^{77}$As, $^{67}$Cu, $^{47}$Sc, and $^{177}$Lu.

In an embodiment of the present invention the linker is a chelating linker and the radionuclide is $^{177}$Lu.

An aspect of the present invention relates to a pharmaceutical composition comprising a radioimmunoconjugate of the present invention, and a pharmaceutically acceptable carrier.

In an embodiment of the present invention the pharmaceutical composition of the present invention comprises one or more additional antibodies or radioimmunoconjugates.

In another embodiment of the present invention one or more additional antibodies or radioimmunoconjugates target CD20.

A further embodiment of the present invention relates to a pharmaceutical composition of the present invention for treating B-cell malignant cells expressing the CD37 antigen.

In an embodiment of the present invention the pharmaceutical composition is for treatment of non-Hodgkin lymphoma and chronic lymphocytic leukemia.

An aspect of the present invention relates to the use of the radioimmunoconjugate of the present invention for the treatment of B-cell malignancies.

An embodiment of the present invention relates to the use of the radioimmunoconjugate of the present invention administered in combination with or in addition to other therapy.

In an embodiment of the present invention the therapy is selected from pretreatment, chemotherapy, monoclonal antibody therapy, surgery, radiotherapy, and/or photodynamic therapy.

In another embodiment of the present invention the therapy comprises pre-treatment using anti-CD20 and/or anti-CD37 monoclonal antibody prior to the treatment with the radioimmunoconjugate of the present invention.

An aspect of the present invention relates to a method for treatment of a B-cell malignancy selected from non-Hodgkin lymphoma and chronic lymphocytic leukemia, comprising administration of an effective amount of a pharmaceutical composition of the present invention.

Another aspect of the present invention relates to a kit for the production of the radioimmunoconjugate of the present invention comprising two or more vials, wherein one vial contains a conjugate comprising a chelator linked to a murine monoclonal antibody HH1; and a second vial contains a radionuclide.

An embodiment of the present invention relates to a kit of the present invention, wherein the content of one or several of the vials are either lyophilized or in a solution.

In another embodiment of the present invention the radioimmunoconjugate is generated by mixing the content of the two vials.

DETAILED DESCRIPTION OF THE PREFERRED EMBODIMENT

The present invention relates to the use of antibody HH1 in radioimmunotherapy.

The combination of a metal radionuclide, linker and anti-CD37 monoclonal antibody has surprisingly shown that radiolabeled HH1 has a relevant biodistribution and tumor uptake in a xenograft/nude mouse model.

This is important information that indicates suitability for use in radioimmunotherapy.

Radioimmunoconjugates

The present invention surprisingly shows that the radioimmunoconjugate $^{177}$Lu-HH1 exhibited a significant cytotoxicity on disseminated tumor cells and that $^{177}$Lu-HH1 was more cytotoxic than $^{177}$Lu-rituximab against the tumor cells for a given dosage.

This finding was unexpected since more radioactivity was bound per cell and the retention of the bound radionuclide was similar or better for $^{177}$Lu-rituximab.

This teaches against common knowledge in the field, which is that anti-CD20 antibody is better than anti-CD37 antibody for radioimmunotherapy.

Furthermore, the present work differs from previous notion in that for a beta-emitter, cross-fire, which is not obtainable in disseminated cells, would be essential for obtaining sufficient effect (Henriksen et al., 1997).

The reason for the observed effect is not clear. Data from experiments with various dosages of unlabeled HH1 and rituximab did not indicate any effects from the unlabeled antibodies in the growth assay used.

One possible explanation could be that there are fewer cells with very low antigen density among CD37 vs. CD20 even though CD20 is on average more strongly expressed on the cell line used.

Retention data did not suggest better retention due to internalization of CD37, which would otherwise be a possible explanation, since some internalization has been reported with the CD37 antigen (Press et al, 2001).

Thus, the present invention relates to a radioimmunoconjugate that binds human CD37 comprising murine monoclonal antibody HH1, a linker, and a radionuclide selected from the group consisting of $^{211}$At, $^{213}$Bi, $^{212}$Bi, $^{212}$Pb, $^{225}$Ac, $^{227}$Th, $^{90}$Y, $^{186}$Re, $^{188}$Re, $^{199}$Au, $^{194}$Ir, $^{166}$Ho, $^{159}$Gd, $^{153}$Sm, $^{149}$Pm, $^{142}$Pr, $^{111}$Ag, $^{109}$Pd, $^{77}$As, $^{67}$Cu, $^{47}$Sc, and $^{177}$Lu.

In an embodiment of the present invention the linker is a chelating linker.

In another embodiment of the present invention the radionuclide is $^{177}$Lu.

In yet another embodiment the radionuclide is another beta-emitter or an alpha-emitter.

Figure 2:
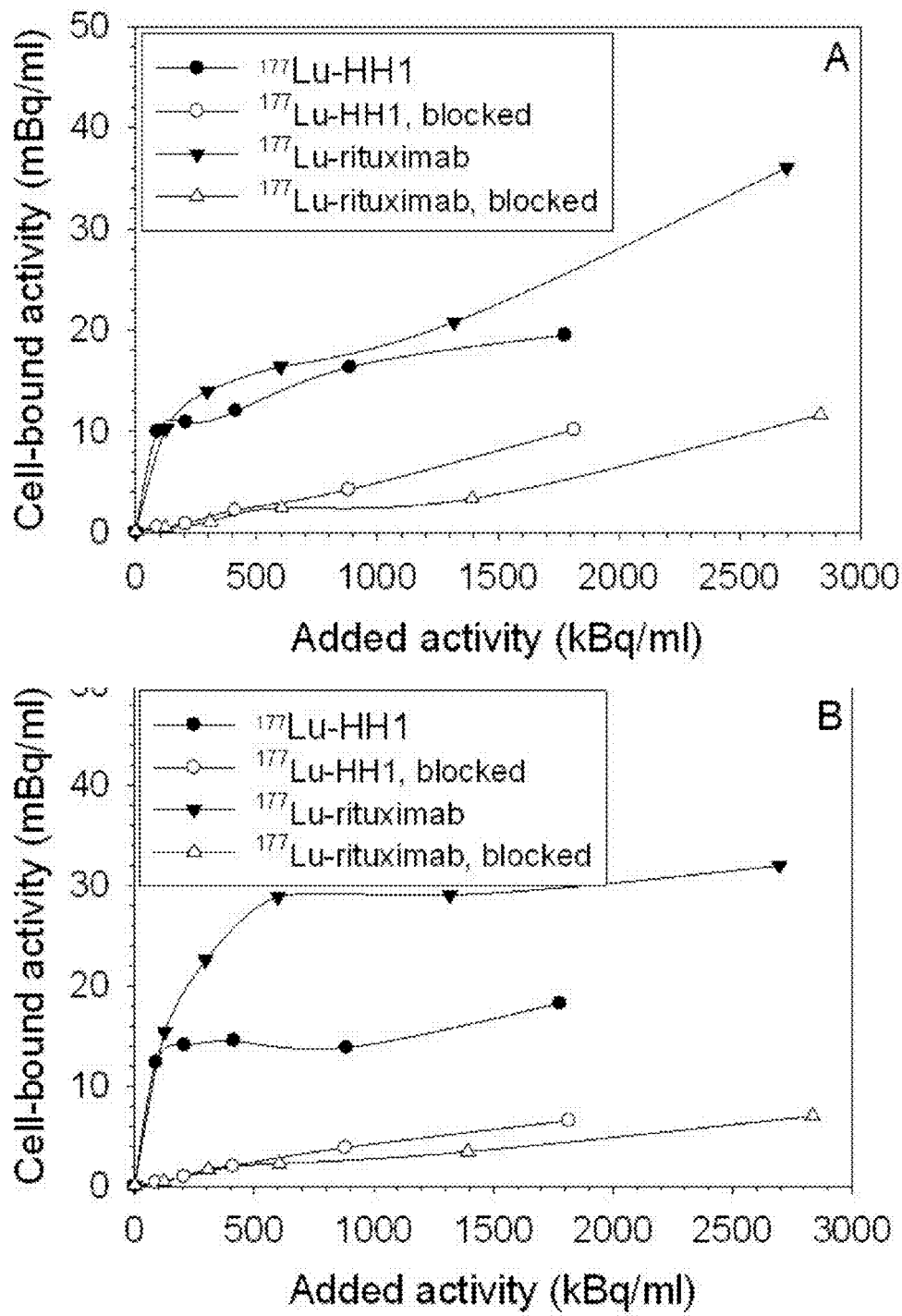
FIG. 2: Activity bound to Daudi cells after incubation with $^{177}$Lu-HH1 or $^{177}$Lu-rituximab for 2 h (A) and 18 h (B). Blocked cells were blocked with 100 µg/ml unlabeled antibody.

The present invention suggests, with in vitro data, that radiolabeled HH1 binds more effectively to the CD37 antigen than radiolabeled rituximab do to the CD20 antigen, i.e., it reached maximum binding to the antigen with less circulating antibody required (Table 2, FIG. 2).

It also required less time to reach maximum binding (FIG. 2). These would be important features in vivo as well because this means that tumor cells can trap the RIC even at lower concentration of circulating antibodies, a situation that may occur in less available areas of solid tumors and for single tumor cells and micrometastases located in remote areas of normal tissues.

This is significantly different from previous data which indicated that higher antibody concentration was required with another anti-CD37 antibody than HH1 (Bernstein et al., 1990), also compared with an anti-CD20 antibody (Press et al., 1993), to saturate antigen and obtain favorable biodistribution.

In addition, the present invention shows that HH1 has some different antigen binding properties compared with a panel of three different anti-CD37 antibodies—despite that all of the antibodies substantially bind to the same epitope.

Blocking experiments, i.e., using cells pre-saturated with unlabeled antibody, showed that HH1 would block the CD37 on living cells from binding to radiolabeled HH1, substantially better than the three other anti-CD37 antibodies.

In a cell assay comparing radiolabeled antibodies, HH1 showed much better immunoreactive fraction compared with the three other antibodies. By immunoreactive fraction is meant the fraction of antibody that can bind antigen if there is an unlimited excess of antigens. Different antibodies can have different ability to preserve the immunoreactivity after going through a labeling procedure. The results in Example 6, Experiment IV, Table 5 shows that the immunoreactivity of HH1 was better preserved than the immunoreactivity of three commercially available antibodies.

On the other hand, immunohistochemistry analyzes showed that the three antibodies stained tissue sections from paraffin-embedded fixed tumor samples, while HH1 failed to do so. Differences in antibody antigen interactions were not detectable by flow cytometry.

Figure 6:
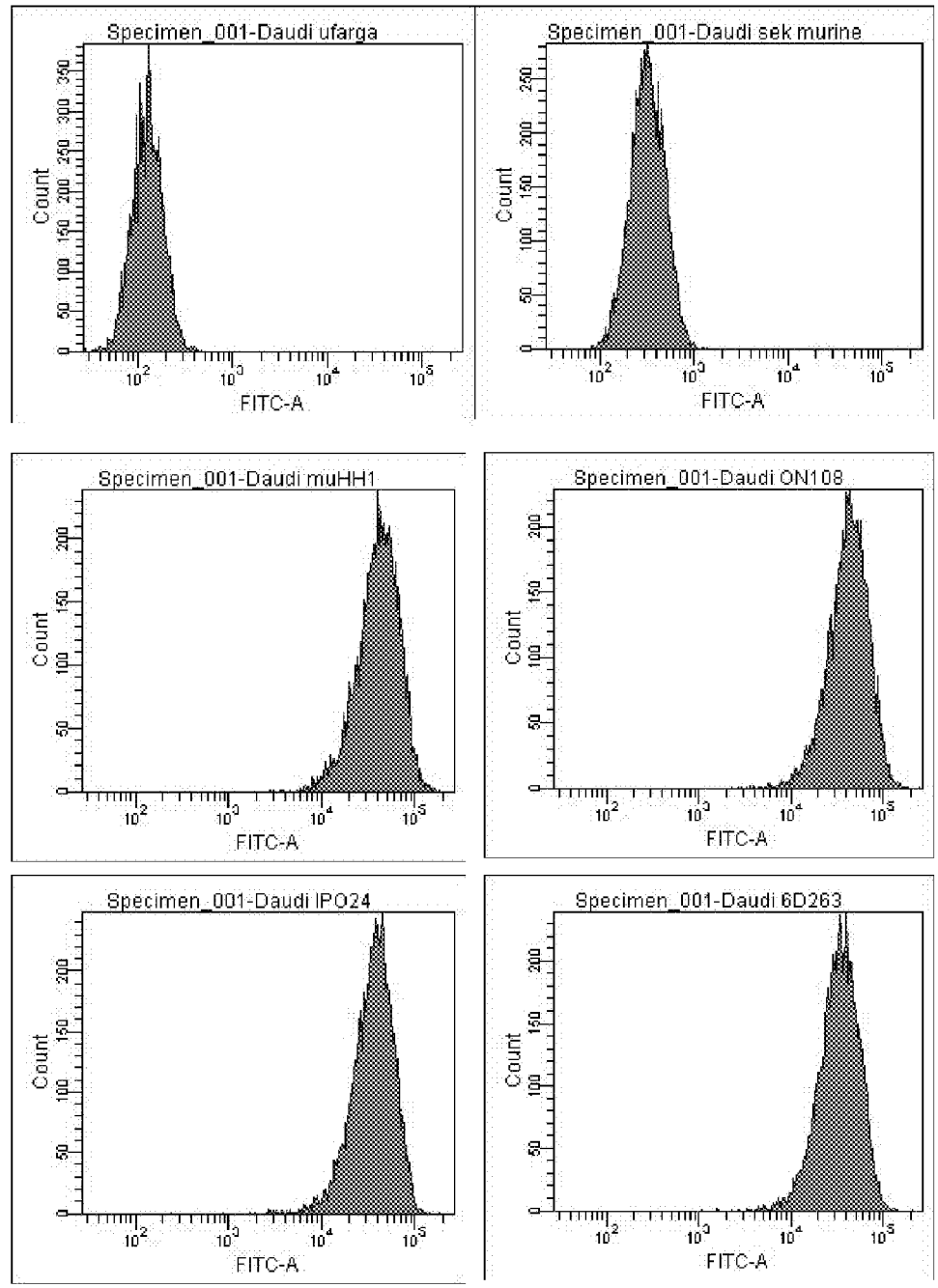
FIG. 6: FITC-histograms of unlabeled Daudi cells, Daudi cells labeled with secondary antibody only, or labeled with HH1, ON.108, IPO.24 or 6D263.

Flow cytometry histograms were similar for HH1 and the three other anti-CD37 antibodies (FIG. 6). All-in-all these data show that HH1 has a significant individual antigen interaction, which in several aspects cannot be predicted from studies with other anti-CD37 antibodies.

The novel anti-CD37 radioimmunoconjugate with strong cytotoxic properties described here consists of the murine monoclonal antibody HH1, a chelating linker, and the beta-emitter $^{177}$Lu.

The radionuclide may be attached to the antibody by first reacting a bifunctional chelator, e.g., p-SCN-bn-DOTA (Macrocyclics, Tex., USA), with the antibody, followed by purification to remove unconjugated chelator, and then reaction of the chelator antibody conjugate with the radionuclide, followed by purification to remove any unconjugated radionuclide.

Alternatively, the chelator and the radionuclide can be combined firstly and subsequently conjugated to the antibody.

Chelating linkers like, e.g., p-SCN-bn-DOTA, can be used for conjugating other metal radionuclides to HH1 in similar fashion to that described for $^{177}$Lu.

Any type of linker with sufficient complexing ability and a functional group allowing direct or indirect conjugation to a protein or a peptide could be used.

Examples of such linkers are described in the literature (e.g. Brechbiel, 2008; Liu, 2008). Some useful examples are bifunctional cyclic chelators like p-SCN-bn-DOTA, DOTA-NHS-ester; bifunctional linear chelators like p-SCN-Bn-DTPA and CHX-A"-DTPA.

The radionuclides in the present invention will preferably be conjugated to a targeting molecule by using bifunctional chelators.

These could be cyclic, linear or branched chelators. Particular reference may be made to the polyaminopolyacid chelators which comprise a linear, cyclic or branched polyazaalkane backbone with acidic (e.g. carboxyalkyl) groups attached at backbone nitrogens.

Examples of suitable chelators include DOTA derivatives such as p-isothiocyanatobenzyl -1,4,7,10-tetraazacyclododecane-1,4,7,10-tetraacetic acid (p-SCN-Bz-DOTA) and DTPA derivatives such as p-isothiocyanatobenzyl-diethylenetriaminepentaacetic acid (p-SCN-Bz-DTPA), the first being cyclic chelators, the latter linear chelators.

Metallation of the complexing moiety may be performed before or after conjugation of the complexing moiety to the targeting moiety.

The radiolabeling procedure will in general be more convenient in terms of time used etc if the chelator is conjugated to the antibody before the radiolabeling takes place.

The principles of preparing radiolabeled conjugates using chelators attached to antibodies is described broader in e.g. Liu, 2008.

Thus, HH1 can be used to prepare radioimmunoconjugates with differences in radiation properties and effective half-lives.

For example anti-CD37 radioimmunoconjugate consisting of the murine monoclonal antibody HH1, a chelating linker and a beta or alpha emitting radionuclide including, but not limited to, $^{177}$Lh, $^{211}$At, $^{213}$Bi, $^{212}$Bi, $^{212}$Pb, $^{225}$Ac, $^{227}$Th, $^{90}$Y, $^{186}$Re, $^{188}$Re, $^{199}$Au, $^{194}$Ir, $^{166}$Ho, $^{159}$Gd, $^{153}$Sm, $^{149}$Pm, $^{142}$Pr, $^{111}$Ag, $^{109}$Pd, $^{77}$As, $^{67}$Cu, $^{47}$Sc can be prepared and used for preparing pharmaceutical preparations and used in therapeutic applications.

Pharmaceutical Compositions

A radioimmunotherapeutic product based on HH1 would typically be provided as a pharmaceutical composition consisting of a radionuclide, according to the description above, linked via a chelator to the murine monoclonal antibody HH1 dissolved in a buffer solution, which to a substantial degree maintain the chemical integrity of the radioimmunoconjugate and is being physiologically acceptable for infusion into patients.

Thus, an aspect of the present invention relates to a pharmaceutical composition comprising a radioimmunoconjugate of the present invention, and a pharmaceutically acceptable carrier and/or excipient.

Acceptable pharmaceutical carriers include but are not limited to non-toxic buffers, fillers, isotonic solutions, etc. More specifically, the pharmaceutical carrier can be but are not limited to normal saline (0.9%), half-normal saline, Ringer's lactate, 5% Dextrose, 3.3% Dextrose/0.3% Saline. The physiologically acceptable carrier can contain a radiolytic stabilizer, e.g., ascorbic acid, which protect the integrity of the radiopharmaceutical during storage and shipment.

One embodiment of the present invention comprises the pharmaceutical composition of the present invention and one or more additional antibodies or radioimmunoconjugates. Antibodies include but are not limited to Rituximab, Epratuzumab, L19, F8, F16, Galiximab, Toralizumab, Alemtuzumab, Ofatumumab, Veltuzumab, Afutuzumab, Tositumomab, Reditux and Ibritumomab. Radioimmunoconjugates include but are not limited to Zevalin and Bexxar.

In another embodiment of the present invention one or more additional antibodies or radioimmunoconjugates target CD20. Antibodies include but are not limited to Rituximab, Veltuzumab, Ofatumumab, Afutuzumab, Tositumomab, Reditux and Ibritumomab. Radioimmunoconjugates include but are not limited to Zevalin and Bexxar.

A further embodiment of the present invention relates to a pharmaceutical composition of the present invention for treating B-cell malignant cells expressing the CD37 antigen.

In an embodiment of the present invention the pharmaceutical composition is for treatment of non-Hodgkin lymphoma and chronic lymphocytic leukemia.

Sequence Identity

As commonly defined "identity" is here defined as sequence identity between genes or proteins at the nucleotide or amino acid level, respectively.

Thus, in the present context "sequence identity" is a measure of identity between proteins at the amino acid level and a measure of identity between nucleic acids at nucleotide level.

The protein sequence identity may be determined by comparing the amino acid sequence in a given position in each sequence when the sequences are aligned.

Similarly, the nucleic acid sequence identity may be determined by comparing the nucleotide sequence in a given position in each sequence when the sequences are aligned.

To determine the percent identity of two nucleic acid sequences or of two amino acids, the sequences are aligned for optimal comparison purposes (e.g., gaps may be introduced in the sequence of a first amino acid or nucleic acid sequence for optimal alignment with a second amino or nucleic acid sequence). The amino acid residues or nucleotides at corresponding amino acid positions or nucleotide positions are then compared.

When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In one embodiment the two sequences are the same length.

One may manually align the sequences and count the number of identical nucleic acids or amino acids. Alternatively, alignment of two sequences for the determination of percent identity may be accomplished using a mathematical algorithm. Such an algorithm is incorporated into the NBLAST and XBLAST programs. BLAST nucleotide searches may be performed with the NBLAST program, score=100, wordlength=12, to obtain nucleotide sequences homologous to a nucleic acid molecules of the invention. BLAST protein searches may be performed with the XBLAST program, score=50, wordlength=3 to obtain amino acid sequences homologous to a protein molecule of the invention.

To obtain gapped alignments for comparison purposes, Gapped BLAST may be utilized. Alternatively, PSI-Blast may be used to perform an iterated search which detects distant relationships between molecules. When utilizing the NBLAST, XBLAST, and Gapped BLAST programs, the default parameters of the respective programs may be used. Alternatively, sequence identity may be calculated after the sequences have been aligned e.g. by the BLAST program in the EMBL database.

Generally, the default settings with respect to e.g. "scoring matrix" and "gap penalty" may be used for alignment. In the context of the present invention, the BLASTN and PSI BLAST default settings may be advantageous.

The percent identity between two sequences may be determined using techniques similar to those described above, with or without allowing gaps. In calculating percent identity, only exact matches are counted.

An embodiment the invention relates to an isolated nucleic acid comprising a sequence sharing 80% sequence identity with the HH1 antibody VH sequence (SEQ ID NO: 1) and/or VL sequence (SEQ ID NO: 3).

An embodiment the invention relates to an isolated nucleic acid comprising a sequence with the HH1 antibody VH sequence (SEQ ID NO: 1) and/or VL sequence (SEQ ID NO: 3).

In another embodiment of the invention the isolated nucleic acid comprises a sequence sharing at least 90% sequence identity with the HH1 antibody VH sequence (SEQ ID NO: 1) and/or VL sequence (SEQ ID NO: 3), such as 90% identity, 91% identity, 92% identity, 93% identity, 94% identity, 95% identity, 96% identity, 97% identity, 98% identity, or 99% identity.

Another embodiment of the invention relates to an antibody comprising a polypeptide sequence sharing 80% sequence identity with the HH1 antibody VH sequence (SEQ ID NO: 2) and/or VL sequence (SEQ ID NO: 4).

Another embodiment of the invention relates to an antibody comprising a polypeptide sequence with the HH1 antibody VH sequence (SEQ ID NO: 2) and/or VL sequence (SEQ ID NO: 4).

In another embodiment of the present invention, the antibody comprises a sequence sharing at least 90% sequence identity with the HH1 antibody VH sequence (SEQ ID NO: 2) and/or VL sequence (SEQ ID NO: 4), such as 90% identity, 91% identity, 92% identity, 93% identity, 94% identity, 95% identity, 96% identity, 97% identity, 98% identity, or 99% identity.

Genetic Variation

Genetic variation is caused by variation in the order of bases in the nucleotides in genes. This variation cause mutations in the genes and subsequently in the proteins that such genes encode.

These mutations can be either sense or mis sense mutations or substitutions.

An embodiment of the present invention relates to the isolated nucleic acid sequence of the HH1 monoclonal antibody VH chain (SEQ ID NO: 1) and/or VL chain (SEQ ID NO: 3) that comprises at least 50, such as 20, such as 10, such as 5, such as 4, such as 3, such as 2, such as 1 sense mutations.

Another embodiment of the present invention relates to the isolated nucleic acid sequence of the HH1 monoclonal antibody VH chain (SEQ ID NO: 1) and/or VL chain (SEQ ID NO: 3) that comprises 0-50, such as 1-50, such as 0-20, such as 1-20, such as 0-10, such as 1-10, such as 0-5, such as 1-5, such as 3, such as 1 sense mutations.

A missense mutation (a type of nonsynonymous mutation) is a point mutation in which a single nucleotide is changed, resulting in a codon that codes for a different amino acid (mutations that change an amino acid to a stop codon are considered nonsense mutations, rather than missense mutations). A missense mutation can render the resulting protein non-functional.

However, not all missense mutations lead to appreciable protein changes. An amino acid may be replaced by an amino acid of very similar chemical properties, in which case, the protein may still function normally; this is termed a neutral, "quiet", or conservative mutation.

Alternatively, the amino acid substitution could occur in a region of the protein which does not significantly affect the protein secondary structure or function. When an amino acid may be encoded by more than one codon (so-called "degenerate coding") a mutation in a codon may not produce any change in translation; this would be a synonymous mutation (a form of silent mutation) and not a missense mutation.

An embodiment of the present invention relates to an antibody comprising a polypeptide sequence of the HH1 monoclonal antibody VH chain (SEQ ID NO: 2) and/or VL chain (SEQ ID NO: 4) that comprises at least 50, such as 20, such as 10, such as 5, such as 4, such as 3, such as 2, such as 1 missense mutations.

An embodiment of the present invention relates to an antibody comprising a polypeptide sequence of the HH1 monoclonal antibody VH chain (SEQ ID NO: 2) and/or VL chain (SEQ ID NO: 4) that comprises 0-50, such as 1-50, such as 0-20, such as 1-20, such as 0-10, such as 1-10, such as 0-5, such as 1-5, such as 3, such as 1 missense mutations.

A conservative substitution is a substitution of one amino acid with another with generally similar properties such that the overall functioning is likely not to be seriously affected.

In another embodiment of the present invention are the mis sense mutations conservative mutations or substitutions.

A further embodiment of the present invention relates to an isolated nucleic acid sequence or a polypeptide sequence with 80% sequence identity to the variable heavy chain (SEQ ID NO: 2) and/or variable light chain (SEQ ID NO: 4) sequences of HH1, wherein the sequence variation is conservative substitutions.

In another embodiment of the present invention is the sequence identity 80% identity, such as 90% identity, 91% identity, 92% identity, 93% identity, 94% identity, 95% identity, 96% identity, 97% identity, 98% identity, or 99% identity and the sequence variation is conservative substitutions.

In order to improve the radiolabeling step it may be beneficial to introduce extra lysine into e.g., the Fc portion of HH1. This could reduce the probability of attaching lysine binding chelators into the antigen combining sites at the antibody, therebye reducing the risk of compromising immunoreactivity during radiolabeling.

Methods for introducing lysine into e.g. the Fc portion of HH1 is known in the art e.g. from Hemminki et al., 1995.

An embodiment of the present invention relates to the radioimmunoconjugate of the present invention which has been modified by 10 Lys in the Fc portion of HH1, such as 8 Lys, such as 6 Lys, such as 5 Lys, such as 4 Lys, such as 3 Lys, such as 2 Lys, such as 1 Lys.

Treatment

Therapeutic use of a pharmaceutical solution according to the present invention may be for treatment against malignant cells expressing the CD37 antigen, including but not limited to non-Hodgkin lymphoma and chronic lymphocytic leukemia.

Other uses could be treatment of autoimmune diseases and treatment of transplantation related effects. The therapy could be based on, but are not limited to, beta-particle-radiation or alpha-particle-radiation or a combination of these.

The therapy could be administered either as a monotherapy or in combination with other therapies, preferentially standard treatments. Such other therapies may be pretreatment, surgery, chemotherapy, immunotherapy, photodynamic therapy, radioimmunotherapy or a combination of two or more of these. By administered is meant intravenous infusion or intravenous injection. More specifically, the radioimmunoconjugate of the present invention can be administered directly in a vein by a peripheral cannula connected to a drip chamber that prevents air embolism and allows an estimate of flow rate into the patient.

In one embodiment the radioimmunoconjugate can be administered in a repeated fashion.

In another embodiment of the present invention the radioimmunoconjugate could be administered in a repeated fashion but with different radionuclides, e.g., beta-radioimmunotherapy could be followed by alpha-radioimmunotherapy or vice versa.

An aspect of the present invention relates to the use of the radioimmunoconjugate of the present invention for the treatment of B-cell malignancies.

An embodiment of the present invention relates to the use of the radioimmunoconjugate of the present invention administered in combination with or in addition to other therapy.

In an embodiment of the present invention the other therapies is selected from pretreatment, chemotherapy, monoclonal antibody therapy, surgery, radiotherapy, and/or photodynamic therapy.

In another embodiment of the present invention the other therapies are bone marrow transplantation or stem cell transplantation and/or therapy.

Another embodiment of the present invention comprises therapeutic pre-treatment using anti-CD20 and/or anti-CD37 monoclonal antibody prior to the treatment with the radioimmunoconjugate of the present invention.

An aspect of the present invention relates to a method for treatment of a B-cell malignancy selected from non-Hodgkin lymphoma and chronic lymphocytic leukemia, comprising administration of an effective amount of the pharmaceutical composition of the present invention.

In an embodiment of the present invention the antibody dosing is 1-1000 mg per patient, more preferably 5-50 mg per patient, and $^{177}$Lu amounting to 1-200 MBq/kg, more preferably 10-100 MBq/kg of bodyweight.

Kits

An aspect of the present invention relates to a kit for the production of the radioimmunoconjugate of the present invention comprising two or more vials, wherein one vial contains a conjugate comprising a chelator linked to a murine monoclonal antibody HH1; and a second vial contains a radionuclide.

A kit may require some procedures to be performed, e.g., radiolabeling and/or purification to take place before infusion.

An embodiment of the present invention relates to a kit of the present invention, wherein the content of one or several of the vials are either lyophilized or in a solution.

By mixing the contents of the two vials to generate the radioimmunoconjugate the final product will appear. Thus, in another embodiment of the present invention the radioimmunoconjugate is generated by mixing the content of the two vials.

This product may need purification prior to use.

EXAMPLES

Example 1

Radiolabeling of HH1

Iodination: Antibodies were labeled with $^{125}$I through indirect iodination using IODOGEN pre-coated iodination tubes (Pierce, Rockford, Ill.) according to the manufacturer's description.

Labeling with $^{111}$In and $^{177}$Lu: Antibodies were first reacted with a chelator (p-SCN-Bn-DTPA or p-SCN-Bn-DOTA).

The DTPA or DOTA chelator was dissolved in 0.05 M HCl, and then added to the antibody, which was pH-adjusted to ca. 8 by washing with carbonate buffer, in a 5:1 ratio. pH was then checked again and if necessary adjusted. The solution was shaken in 60 min at room temperature, and then the reaction was terminated by adding 50 µl 200 mM glycine solution (per mg antibody). To remove free chelator the conjugated antibody was washed 4-5 times with PBS (PAA), and then adjusted to pH 5 by washing with ammonium acetate. $^{111}$In or $^{177}$Lu (Perkin Elmer, Boston, Ma, USA) was then added to 0.5 mg DOTA-Ab, and shaken for one hour at 42° C. Finally, the product was purified by elution on a gel filtration column, e.g., Sephadex G-25 PD10 (GE health) or similar. The overall labeling yield varied from 17% to 63%.

The quality of the radioimmunoconjugates was measured using lymphoma cells and a modified Lindmo method. Cell concentrations up to 108 cells pr ml were used to compensate for the modest specific activity of $^{111}$In-conjugates. For $^{125}$I-conjugates (which have a higher specific activity) it was enough to use cell concentrations up to $4*10^7$ cells pr ml.

The immunoreactivity and specific activity for the radioimmunoconjugates can be seen in Table 1.

Example 2

Binding Parameters

The association rate constant, $k_a$, the equilibrium dissociation constant, $K_d$, and the mean number of binding sites, $B_{max}$, was determined by a one-step curve fitting method (Dahle et al. 2007). The binding parameters were measured for HH1 and rituximab and for three different lymphoma cell lines; Raji, Rael and Daudi cells (Table 2). Specific binding was measured as a function of time and antibody concentration, and the solution of the differential equation describing the net rate of formation of the antigen-antibody complex was fitted to the experimental data points using the association rate constant, $k_a$, the equilibrium dissociation constant, $K_d$, and the mean number of binding sites, $B_{max}$, as parameters. Five million cells pr ml were used, four concentrations of $^{125}$I-labeled antibody (100 ng/ml, 1000 ng/ml, 5000 ng/ml and 10000 ng/ml) and 7 incubation time points (5 min, 10 min, 20 min, 30 min, 1 h, 1.5 h and 2 h). After incubation, cells were washed twice with PBS, and then counted in a gamma counter.

Example 3

Retention of Cell-Bound Antibody

Figure 1:
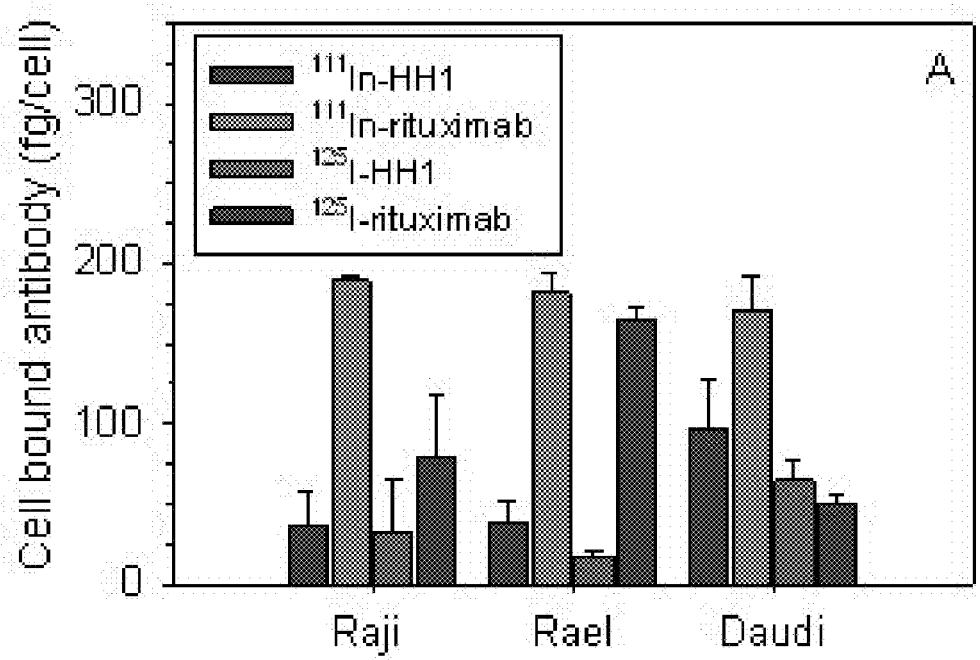
FIG. 1: Cell-bound antibody immediately (A) and 96 hours (B) after washing for incubation of Raji, Rael and Daudi cells with $^{111}$In-HH1, $^{111}$In-rituximab, $^{125}$I-HH1 and $^{125}$I-rituximab.
Figure 1:
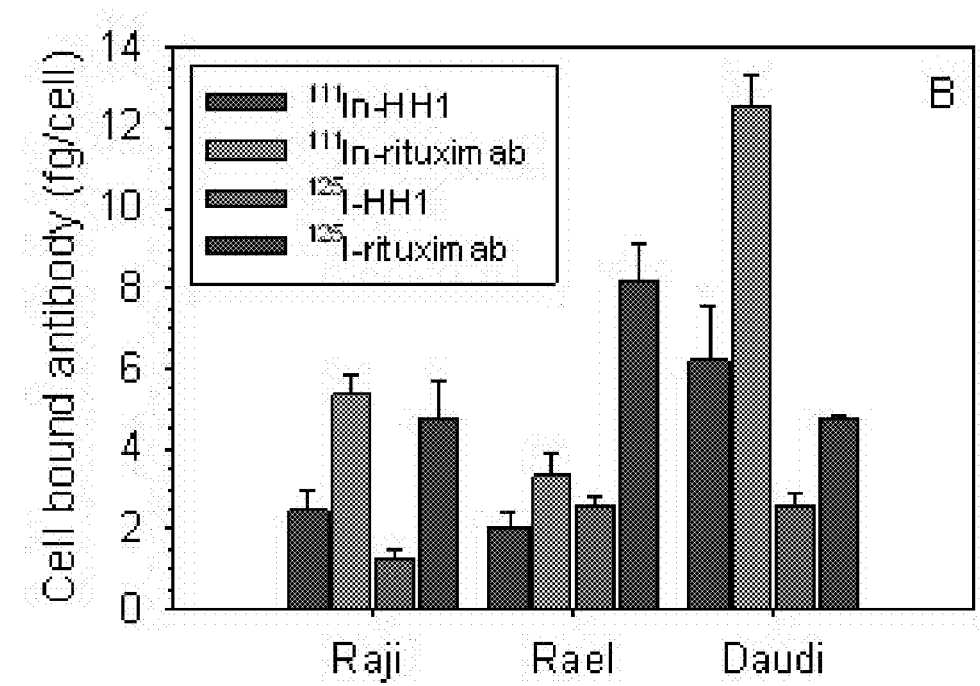

Retention of cell-bound antibody immediately and 96 hours after washing were measured after incubation of Raji, Rael and Daudi cells with $^{111}$In-HH1, $^{111}$In-rituximab, $^{125}$I-HH1 and $^{125}$I-rituximab (FIG. 1).

One million cells in 1 ml RPMI 1640 medium with 10% foetal calf serum, 1% L-glutamine and 1% penicillin/streptomycin were incubated with 1 µg/ml $^{125}$I or $^{111}$In-labeled HH1 or rituximab for one hour, washed twice with medium and incubated further for four days. The cell bound activity was determined immediately after washing (FIG. 1A) and after four days of incubation (FIG. 1B) by measuring the number of cells (Vi Cell Viability Analyzer, Beckman Coulter, Fullerton, Calif., USA) and the amount of radioactivity with a calibrated gamma detector (Cobra II auto-gamma detector, Packard Instrument Company, Meriden, Conn., USA).

Example 4

Treatment of Lymphoma Cells In Vitro with $^{177}$Lu-HH1 or $^{177}$Lu-Rituximab Experiment I: Binding of $^{177}$Lu-HH1 to Daudi Cells One ml of Daudi cell suspension (1 million cells/ml) was seeded in 24 tubes and half of the tubes were blocked with 100 µg/ml of either HH1 or rituximab and incubated for 30 minutes at 37° C. Subsequently, each tube was added either $^{177}$Lu-HH1 or $^{177}$Lu-rituximab to a final concentration of 0, 1, 2.5, 5, 10 or 20 µg/ml and incubated further at 37° C. The specific activity was 91.6 kBq/µg for $^{177}$Lu-HH1 and 136.6 kBq/µg for $^{177}$Lu-rituximab.

The amount of added activity was measured during the incubation period with a gamma detector (Cobra II auto-gamma detector, Packard Instrument Company). After 2 hours, half of the cells were washed and cell bound activity was measured (FIG. 2A) while half of the cells were incubated over night (18 h) before washing and measurement of cell bound activity (FIG. 2B).

There was no difference between cells incubated with HH1 and cells incubated with rituximab after 2 hour incubation, while the cell bound activity was twice as high for cells incubated with rituximab than for cells incubated with HH1 after 18 hour incubation (FIG. 2).

Tables 3 and 4 indicate that radiolabeled HH1 saturates the antigen quicker and at lower antibody concentration than rituximab. The nonspecific binding seems to be similar for the two radioimmunoconjugates (RIC), and it increases with increasing concentration of RIC in the medium.

The maximum number of specific bound $^{177}$Lu was about twice as high for rituximab as for HH1. However at the 1 µg/ml dosage, there were almost no differences in the number of specifically bound radioactive atoms.

Experiment II: Two Hour Incubation with $^{177}$Lu-IgG: Cell Growth Data

Daudi cells were incubated with radioimmunoconjugates as in experiment I (FIG. 2 A).

Growth of Daudi cells after 2 hour incubation with $^{177}$Lu-HH1 or $^{177}$Lu-rituximab was measured by seeding 50.000 cells from each tube in three wells in six 12-well plates. The amount of cells were measured for several time points the next 14 days using an automatic imaging system (Clone Select Imager, Gentix Ltd, Hampshire, UK).

There was no effect of unlabeled antibody alone on cell growth. However, the blocked cells treated with $^{177}$Lu-antibody clearly did not grow as fast as the untreated control cells, indicating that there was an effect of unbound $^{177}$Lu-antibody or unspecifically bound $^{177}$Lu-antibody on the cells (FIG. 3).

Figure 3:
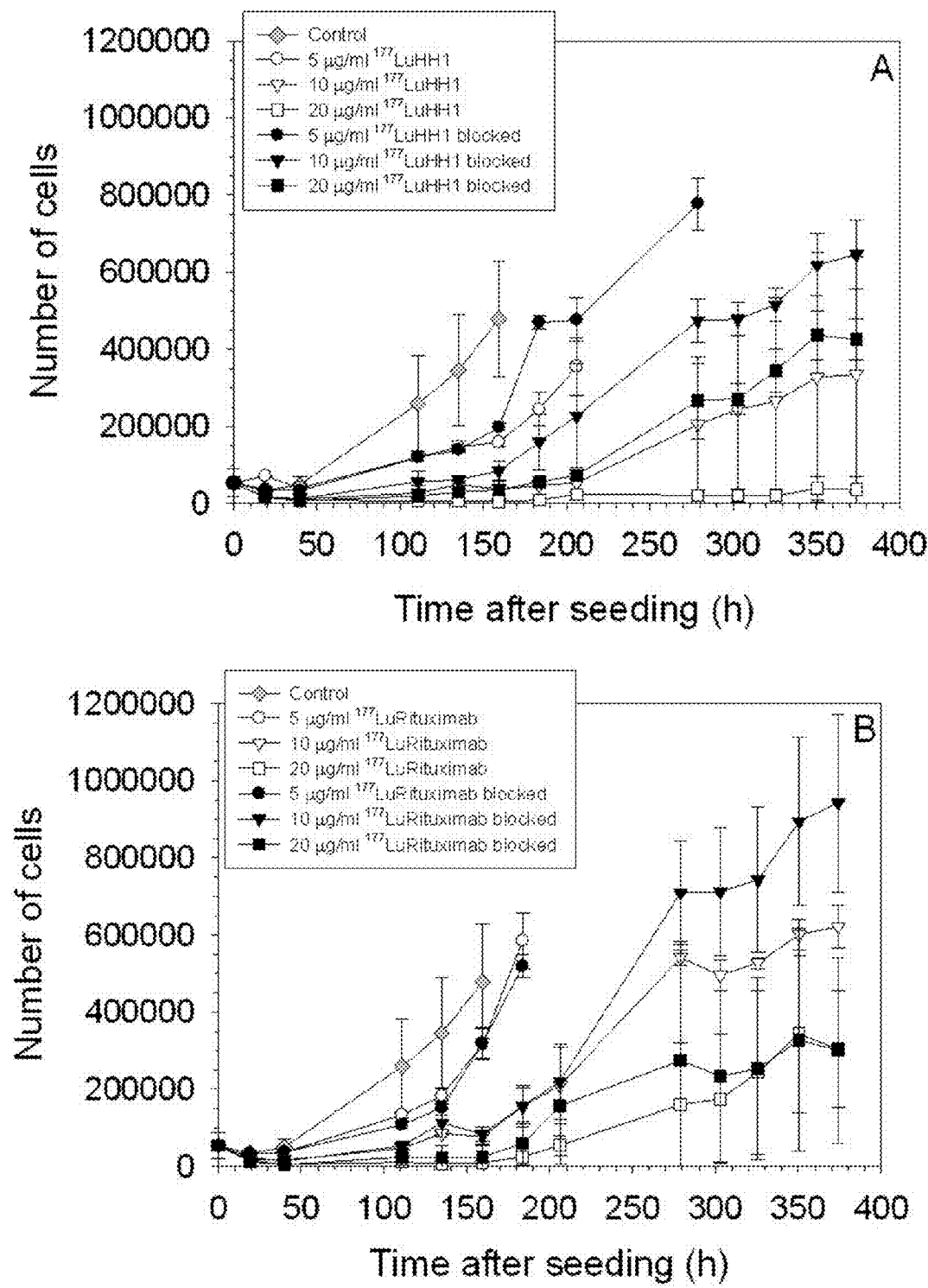
FIG. 3: Growth of Daudi cells incubated with $^{177}$Lu-HH1 (A) or $^{177}$Lu-rituximab (B) for 2 h before washing.

Treatment of unblocked cells with $^{177}$Lu-antibody resulted in an increase in growth delay of 44% for cells treated with 10 µg/ml $^{177}$Lu-HH1 (FIG. 3 A) and of 31% for cells treated with 10 µg/ml $^{177}$Lu-rituximab (FIG. 3 B).

For treatment with 20 µg/ml the difference between the two antibodies was even larger since there was no regrowth of the cells treated with $^{177}$Lu-HH1. This result was unexpected since the cells were labeled with the same amount of antibody (FIG. 2 A).

Experiment III: Eighteen Hour Incubation with $^{177}$Lu-IgG: Cell Growth Data

Daudi cells were incubated with radioimmunoconjugates as in experiment I (FIG. 2 B). Growth of Daudi cells after 18 hour incubation with $^{177}$Lu-HH1 or $^{177}$Lu-rituximab was measured by seeding 50.000 cells from each tube in three wells in six 12-well plates.

The amount of cells were measured for several time points the next 14 days using an automatic imaging system (Clone Select Imager, Gentix Ltd, Hampshire, UK). There was no effect of unlabeled antibody alone on cell growth.

The inhibition of cell growth on the blocked cells treated with $^{177}$Lu-antibody was larger in this experiment (FIG. 4) than in experiment II (FIG. 3) because of 16 hour increased incubation time with radioimmunoconjugate in the medium.

Figure 4:
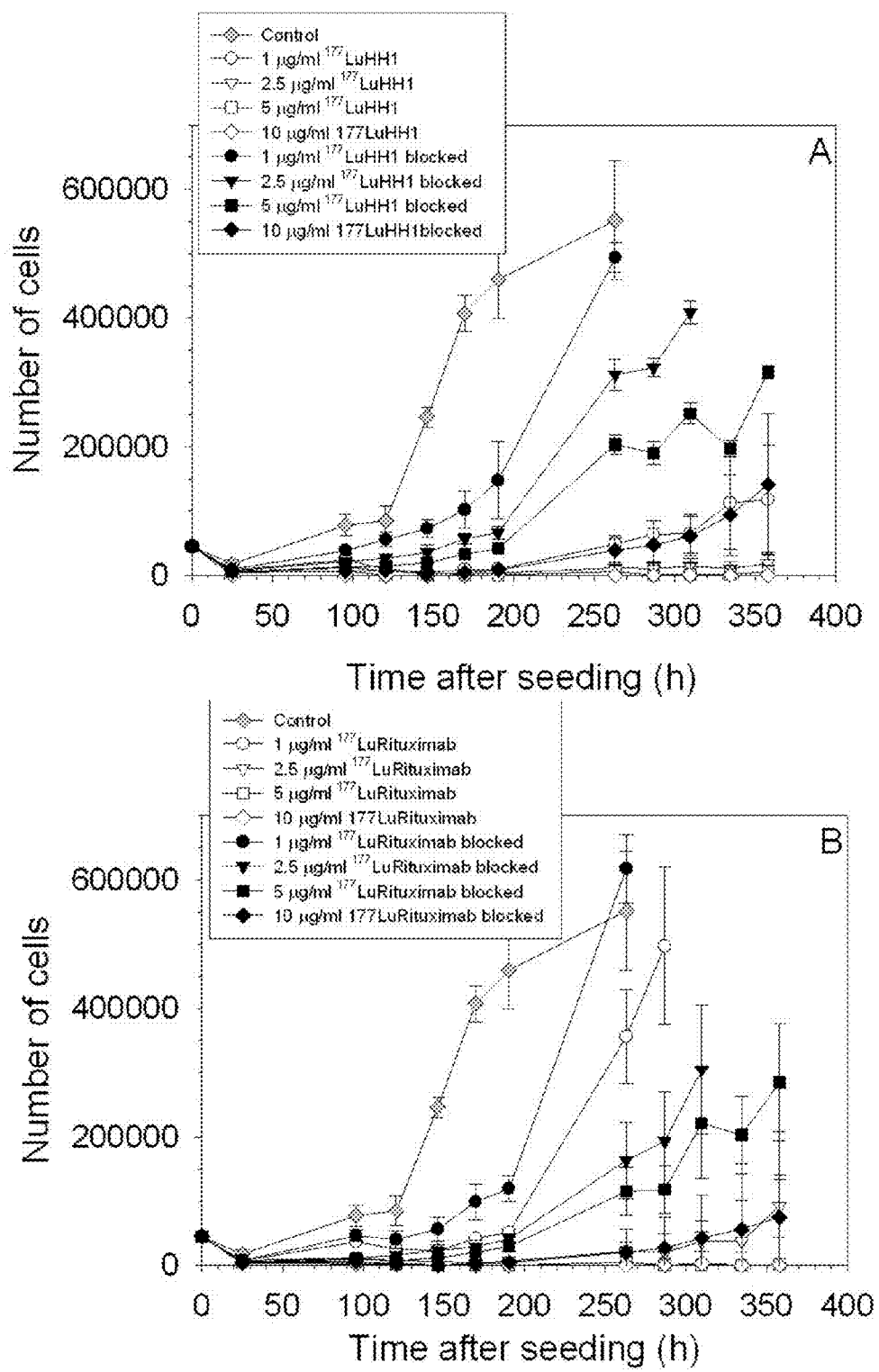
FIG. 4: Growth of Daudi cells incubated with $^{177}$Lu-HH1 (A) or $^{177}$Lu-rituximab (B) for 18 h before washing.

Treatment of unblocked cells with $^{177}$Lu-antibody resulted in an increase in growth delay of 107% for cells treated with 2.5 µg/ml $^{177}$Lu-HH1 (FIG. 4 A) and of 52% for cells treated with 2.5 µg/ml $^{177}$Lu-rituximab (FIG. 4 B). This result was unexpected since after 18 h of incubation the cells labeled with $^{177}$Lu-rituximab had twice as much cell-bound activity attached than the cells labeled with $^{177}$Lu-HH1 (FIG. 2 B).

Example 5

Biodistribution of HH1

Biodistribution of $^{111}$In-labeled HH1 was studied in BALB/c-nude (nu/nu) mice with Daudi xenografts with size 32-256 mm$^3$ at the start of the study.

The radiolabeling was performed using pSCN-Bz-DOTA as a bifunctional chelating agent to complex the radionuclide and attach it to the antibody (see Example 1). The preparation was administered by tail vein injection of 100 µl solution to each animal.

An activity of 120 kBq was injected in each animal. Five animals were used per time point. Autopsies were performed after cervical dislocation at various time points after injection. The weight of each tissue sample was determined, and $^{111}$In were measured by a calibrated gamma detector (Cobra II auto-gamma detector, Packard Instrument Company, Meriden, Conn., USA). Samples of the injectates were used as references in the measurement procedures.

Figure 5:
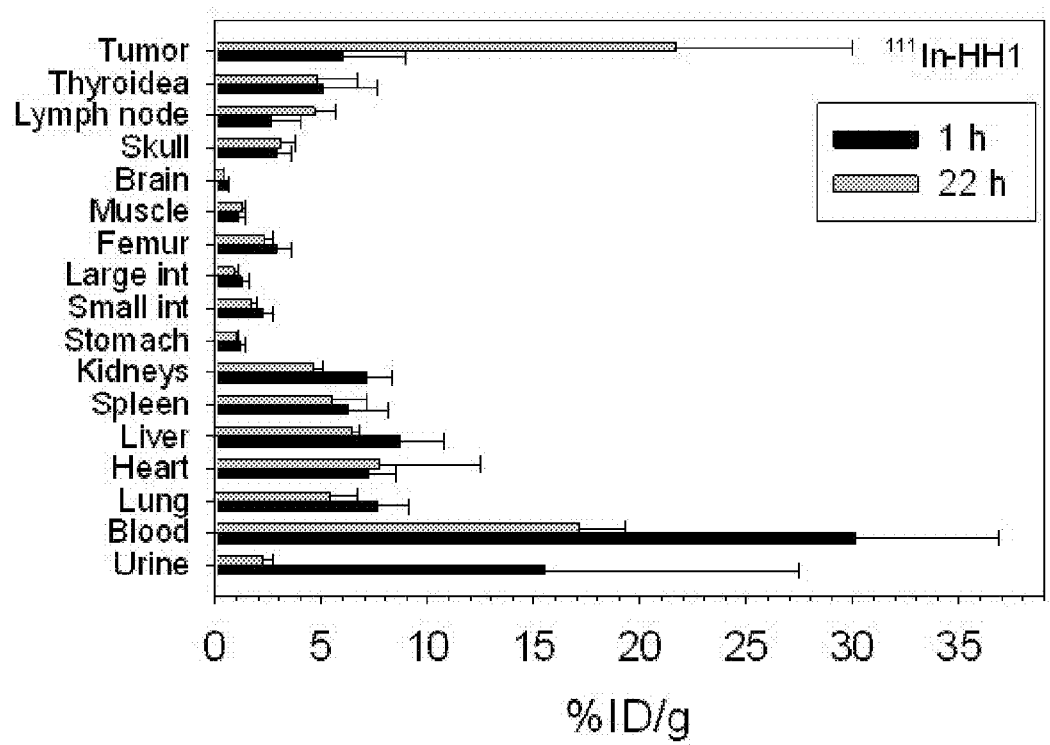
FIG. 5: Biodistribution of $^{111}$In-labeled via chelator to HH1 in mice with Daudi xenografts.

The uptake of $^{111}$In-HH1 24 hours after injection of mice with Daudi xenografts and the biodistribution in normal tissues are presented in FIG. 5. The radiolabeled antibody has a relevant tumor targeting and biodistribution. The chelator-conjugate $^{111}$In-HH1 shows good stability in vivo.

Example 6

Comparison of HH1 with Three Other Anti-CD37 Antibodies

Experiment I: Antigen Blocking Ability of Anti-CD37 Antibodies Against Radiolabeled HH1

To test whether the HH1 antigen interaction can be blocked by other anti-CD37 antibodies, Daudi cells were blocked by pre-incubation with either HH1, O.N.108, IPO-24 or 6D263 antibodies. Daudi cells (2 millions/ml) were incubated for 15 minutes with either HH1, O.N.108, IPO-24 or 6D263 antibodies (20 µg/ml) and added $^{125}$I-labeled HH1 antibody and incubated for 1 hour.

Thereafter, the cells were centrifuged and washed 3 times and the activities in supernatant and cell pellets were counted using a X-ray/gamma counter. Compared with the HH1 blocked cells, the bound fraction of $^{125}$I-labeled HH1 was 48%, 44% and 51% higher for O.N.108, IPO-24 or 6D263 blocked cells, respectively.

Thus, the antigen binding of $^{125}$I-HH1 was better blocked with HH1 than with the three other antibodies suggesting some differences in antigen interaction. In conclusion, HH1 has significant different antigen-binding properties compared with a panel of three other anti-CD37 monoclonal antibodies.

Experiment II: Antibody Binding to Paraffin Embedded Lymphoma Tissue Samples

To compare the ability of HH1 and three commercially available CD37 antibodies to bind to fixated lymphoma samples, biopsies from lymphoma patients were fixed in formalin, embedded in paraffin and cut in 10 µm slices that were mounted on object glasses.

The samples were labeled with the antibodies HH1, IPO.24, ON.108 and 6D263 and the grade of labeling was detected using rabbit anti mouse polyclonal antibody and peroxidase staining.

The antibodies IPO.24 and ON.108 resulted in the strongest labeling of the lymphoma samples. The 6D263 antibody labeled the sample a little weaker. The HH1 antibody labeling of the sections was insignificant.

Thus, it can be concluded, since HH1 did not bind while three other anti-CD37 antibodies were binding, that HH1 has a significantly different antigen interaction.

Experiment III: Flow Cytometry of HH1, IPO.24, ON.108 and 6D263 Antibodies

To investigate differences in antigen expression detected by the different CD37 antibodies vs. HH1 Daudi cells were washed twice with RPMI 1640 medium with 5% foetal calf serum and labeled with 10 µg/ml of the primary antibodies HH1, IPO.24, ON.108 and 6D363 for 0.5 hour in 0.2 ml medium with 10% FCS on ice.

Subsequently, the cells were washed twice with PBS with 0.25% FCS and labeled with FITC-labeled polyclonal rabbit anti-mouse IgG Fab'2 (diluted 1:20) (FIG. 6) for 0.5 hour on ice. Fluorescence from the FITC-label was detected by exciting with a 488 nm laser in a flow cytometer.

Dead cells and doublets were gated away using forward scatter, side scatter and propidium iodide signals. There was no significant variation among the different FITC histograms of the various CD37 antibodies (FIG. 6).

In conclusion, HH1 and the tree other anti-CD37 antibodies IPO.24, ON.108 and 6D363, produce similar flow cytometry histograms.

Experiment IV: The Binding Fraction for HH1 and Three Commercially Available Anti-CD37 Antibodies To compare the binding fraction of HH1 with the O.N.108, IPO-24 or 6D263 antibodies (Santa Cruz Biotechnology) using Daudi cells. Cell suspensions, representing a large antigen excess, consisting of 60 million Daudi cells in 0.2 ml RPMI 1640 medium with 5% foetal calf serum were blocked for 15 minutes with HH1, O.N.108, IPO-24 or 6D263 antibodies (500 µg/ml) to account for non-specific binding of the antibody. Other parallels were unblocked.

Subsequently, $^{125}$I-labeled HH1, O.N.108, IPO-24 or 6D263 antibody (5-10 ng/ml) was added and the cells were incubated for 2 hours at 4° C. with gentle shaking. Thereafter, the cells were centrifuged and washed 2 times with PBS with 1% FCS. The cell pellets were transferred to clean tubes and counted using a gamma counter.

The binding fraction was determined as the difference in activity for the unblocked and the blocked vials vs. the added activity. The HH1 showed a much higher binding fraction compared with the other CD37 antibodies (Table 5). In conclusion, HH1 showed a much higher immunoreactivity against living cells compared with IPO.24, ON.108 and 6D363 when the antibodies were radiolabeled in similar fashion. This result indicates that HH1 has different antigen interaction than the three other antibodies.

Example 7

DNA and Amino Acid Sequence of Low and Heavy Chain Variable Regions

The gene and protein sequence of the variable regions of the HH1 anti-CD37 antibody is as follows:

The VH αCD37 gene sequence corresponds to SEQ ID NO: 1 and the VH αCD37 protein sequence corresponds to SEQ ID NO: 2.

```
VH αCD37
gagatccagctgcagcagtctggacctgagctggtgaagcctggggcttcagtgaaggta
 E   I   Q   L   Q   Q   S   G   P   E   L   V   K   P   G   A   S   V   K   V tcctgcaaggcttctggttactcattcactgactacaacatgtactgggtgaagcagagc
 S   C   K   A   S   G   Y   S   F   T   D   Y   N   M   Y   W   V   K   Q   S catggaaagagccttgagtggattggatatattgatccttacaatggtgatactacctac
 H   G   K   S   L   E   W   I   G   Y   I   D   P   Y   N   G   D   T   T   Y aaccagaagttcaagggcaaggccacattgactgttgacaagtcctccagcacagccttc
 N   Q   K   F   K   G   K   A   T   L   T   V   D   K   S   S   T   A   F atccatctcaacagcctgacatctgaggactctgcagtctattactgtgcaagatcccct
 I   H   L   N   S   L   T   S   E   D   S   A   V   Y   Y   C   A   R   S   P tatggtcactatgctatggactactggggtcaaggaacctcagtcaccgtctcctca
 Y   G   H   Y   A   M   D   Y   W   G   Q   G   T   S   V   T   V   S   S
```

The VL αCD37 gene sequence corresponds to SEQ ID NO:3 and the VL αCD37 protein sequence corresponds to SEQ ID NO: 4.

```
VL αCD37
gacattgtgatgacccagtctcacaaactcttgtccacatcagtaggagacagggtcagc
 D   I   V   M   T   Q   S   H   K   L   L   S   T   S   V   G   D   R   V   S atcacctgcaaggccagtcaggatgtgagtactgctgtagactggtatcaacagaaacca
 I   T   C   K   A   S   Q   D   V   S   T   A   V   D   W   Y   Q   Q   K   P ggacaatctcctaaactactgattaactgggcatccacccggcacactggagtccctgat
 G   Q   S   P   K   L   L   I   N   W   A   S   T   R   H   T   G   V   P   D cgcttcacaggcagtggatctgggacagattatactctcaccatcagcagtatgcaggct
 R   F   T   G   S   G   S   G   T   D   Y   T   L   T   I   S   S   M   Q   A gaagacctggcactttattactgtcgacaacattatagcactccattcacgttcggctcg
 E   D   L   A   L   Y   Y   C   R   Q   H   Y   S   T   P   F   T   F   G   S gggacaaagttggaaataaaa
 G   T   K   L   E   I   K
```

The amino acid sequence is significantly different from the amino acid sequence of the CD37 binding antibody A0 (Heider et al., 2009). The overlap between the variable light chain of HH1 and A0 is 56%, while the overlap between the variable heavy chain is 82%.

Example 8

Binding of Radiolabeled HH1 on Cells Saturated with CD20 Antibody Rituximab

Background

Non-Hodgkin lymphoma patients often receives rituximab as a standard therapy. It would be advantageous if radiolabeled HH1 could be used in patients even if they are undergoing rituximab therapy. Daudi lymphoma cells, which express both the CD20 and the CD37 antigens, were used as a model.

Methods

Daudi lymphoma cells (3, 3 millions in 0.5 ml) were either pre- and co-treated with excessive amounts (100 μg/ml of rituximab) for five minutes and thereafter added 1 μg of $^{125}$I-labeled HH1 or given $^{125}$I-labeled HH1 without rituximab pretreatment. To determine non-specific binding of $^{125}$I-HH1 the same configuration as above but with pretreatment with unlabeled HH1 (10 μg/ml was used). The cells were incubated for two hours in PBS at room temperature and counted in a gamma counter, washed three times in 1 ml PBS followed by centrifugation, and finally recounted for cell bound radioactivity.

Results

With rituximab pre-treatment/co-treatment, 26.0% (total bound, 27.4%—nonspecific bound, 1.4%) of the added $^{125}$I-HH1 bound specifically to the cells.

Without rituximab pre-treatment/co-treatment, 25.5% (26.9-1.4) bound specifically (all numbers represents mean of three parallels). I.e, there were no significant difference in the binding of $^{125}$I-HH1 due to the presence of rituximab.

Conclusion

Pre- and co-treatment with excessive amounts of rituximab did not alter the cell binding ability of radiolabeled HH1 and, thus, did not block the access to the CD37 antigen.

This indicates that radioimmunotherapy with radiolabeled HH1 may be suitable in patients subsequently to or during immunotherapy with anti-CD20 antibody as well as in patients not treated with rituximab.

Example 9

Treatment of SCID Mice Inoculated Intravenously with Daudi Lymphoma Cells using $^{177}$Lu-HH1

Background

Figure 8:
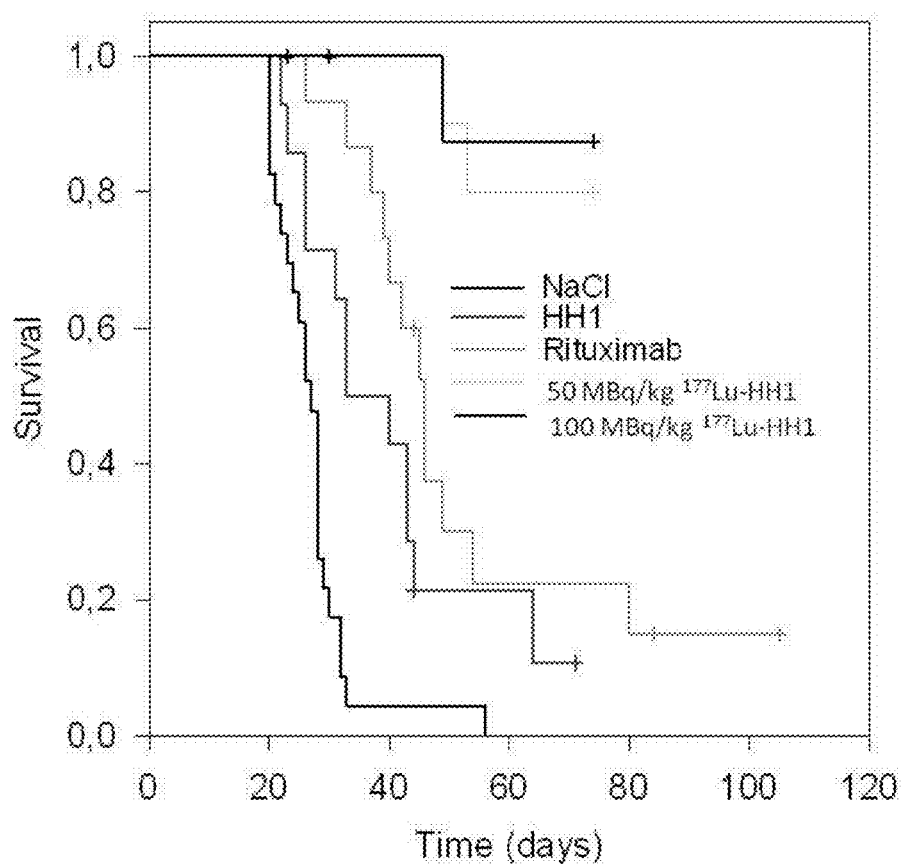
FIG. 8: Therapy of mice with iv injected Daudi cells. Survival of mice treated with 50 and 100 MBq/kg $^{177}$Lu-HH1, cold HH1, cold rituximab and NaCl.

Treatment of lymphoma patients with current CD20 directed radioimmunotherapy can be problematic in patients previously treated with rituximab because of antigenic drift and possible blockage of CD20 antigen. Therefore, radioimmunotherapy targeting other antigens might be more effective. By intravenous injection of human lymphoma cells in severe combined immune deficient (SCID) mice we made an intravenous tumor model. When SCID mice are inoculated intravenously with Daudi lymphoma cells they will develop hind leg paralysis due to the growth of the Daudi tumor cells.
Experimental SCID mice were injected intravenously with 10 million Daudi cells one week before administration of 50 or 100 MBq/kg $^{177}$Lu-HH1, 50 μg HH1, 50 μg rituximab or NaCl. The mice were monitored for hind leg paralysis and body-weight loss as well as WBC count every other week. Discontinuation of symptom-free survival was used as an end point. To prepare the radiolabeled antibody, HH1 was first labeled with p-SCN-Bn-DOTA and purified. After buffer exchange $^{177}$Lu (Perkin Elmer, Boston, Mass., USA) was added to the DOTA-HH1, and shaken for 40 minutes at 40° C. Specific activity was approximately 3200 MBq/mkg for the final product. Each preparation was dissolved in isotonic saline to a total injection volume of 100 μl per animal.
Results Median symptom free survival was 26 days (range 21 to 33) for saline, 40 days (range 23 to 44) for HH1 and 40 days (range 33 to 44) for rituximab (FIG. 8). For 50 kBq/kg $^{177}$Lu-HH1, 80% of the animals were alive after 79 days. Two of the mice in the 100 kBq/g group died before any of the animals in the saline groups, and the blood cell counts indicated radiotoxicity. A third animal in the 100 kBq/g group died at day 49. The other animals (70%) were alive at day 79. The survival of the mice treated with $^{177}$Lu-HH1 were significantly higher than the survival of mice treated with NaCl, HH1 or Rituximab (p<0.005, Mann Whitney Log Rank Test)
Conclusion The data shows that the groups receiving $^{177}$Lu-HH1 in dosages of 50 or 100 kBq/g of b.w. groups had considerably better survival than the groups receiving saline or immunotherapy with either HH1 or rituximab. The toxicity data indicate that the activity should be kept below 100 kBq/g b.w. These data indicate that $^{177}$Lu-HH1 has relevant properties for in vivo radioimmunotherapy.

Example 10

Biodistribution of $^{177}$Lu-HH1 in Nude Mice with CD37 Expressing Tumor Xenografts Background Lutetium-177 labeled HH1 antibody was evaluated for in vivo tissue distribution and tumor targeting.
Experimental Procedure
Labeling of Antibodies with Radionuclides The antibody was first labeled with the chelator p-SCN-Bn-DOTA. DOTA was dissolved in 0.05M HCl, added to the antibody in a 5:1 ratio and pH-adjusted to 8-9 by washing with carbonate buffer using Amicon centrifuge filters (Millipore, USA) with a molecular weight cut-of 30 kDa.

Figure 7:
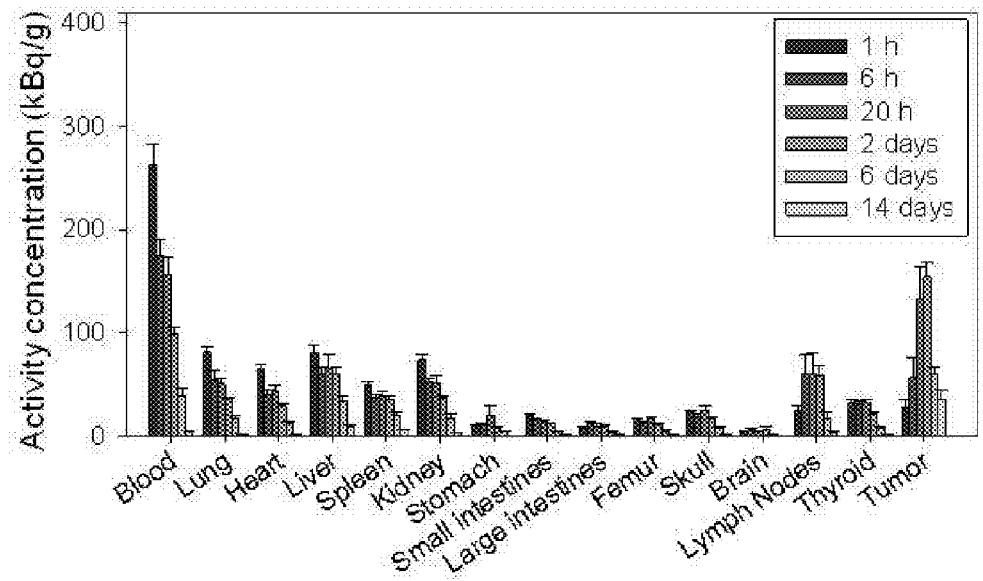
FIG. 7: Biodistribution of $^{177}$Lu-in female nude mice with Daudi tumor.

The pH was then checked again and if necessary adjusted. The solution was shaken during 60 min at room temperature, and then the reaction was terminated by adding 50 μl 200 mM glycine solution (per mg antibody). To remove free chelator the conjugated antibody was washed 4-5 times with PBS (PAA) (using Amicon and centrifugation), and then adjusted to pH 5 by washing with ammonium acetate. $^{177}$Lu (Perkin Elmer, Boston, Mass., USA) was then combined with 0.5 mg DOTA-HH1 in a 2 ml polypropylene tube (Eppendorf, Germany), and shaken for one hour at 40° C. Specific activities were typically 25-120 MBq/kg for $^{177}$Lu-conjugates.
Immunoreactivity The quality of the radioimmunoconjugates were measured using lymphoma cells and a modified Lindmo method. Cell concentrations up to 108 cells pr ml were used. The conjugates used in the experiments had immunoreactivity above 50%.
Biodistribution of Radioimmunoconjugates Biodistributions of $^{177}$Lu-HH1 was determined in male BALB/c nude (nu/nu) mice implanted with 1.1.1 mm Daudi tumor xenografts three weeks before. The preparations were administered by tail vein injection of 100 μl solution in each animal. A mean activity of 500 kBq per mice for $^{177}$Lu-HH1. Four to five animals were used per time point. Autopsies were performed after cervical dislocation at various time points after injection. The weight of each tissue sample was determined, and $^{177}$Lu were measured by a calibrated gamma detector (Cobra II auto-gamma detector, Packard Instrument Company, Meriden, Conn., USA). Samples of the injectates were used as references in the measurement procedures.
Results and Discussion Uptake and retention of $^{177}$Lu-labeled HH1 and in normal tissues of BALB/c-nude (nu/nu) female mice with Daudi xenografts are presented in FIG. 7. There were no signs of redistribution of nuclide from/to any organs after the initial uptake of radioimmunoconjugates, which indicate that the radioimmunoconjugates were stable.

Injection of $^{177}$Lu-HH1 in nude mice with tumor showed a low uptake in bone. Free $^{177}$Lu is known to accumulate in bone so this result indicates that the radioimmunoconjugate was stable in vivo. The uptake in the tumors was significantly higher than in other organs at later time points.

This indicates that $^{177}$Lu has relevant half life for radioimmunotherapy using the HH1 antibody.

The biodistribution data of $^{177}$Lu-HH1 show a relevant normal tissue uptake and clearance and significant retention in CD37 expressing tumor xenografts.

The HH1 antibody seems to be well suited for radioimmunotherapy. The $^{177}$Lu-HH1 conjugate seems particularly suitable, as favorable tumor to normal tissue ratios were obtained before a larger fraction of the radionuclide was decayed.
Tables

TABLE 1

Immunoreactivity and specific activity for the radioimmunoconjugates.

| Radioimmunoconjugate | IRF[1] (%) | Specific activity[1] (MBq/mg) | # exp. |
|---|---|---|---|
| $^{125}$I-HH1 | 66 ± 17 (39-92) | 75 ± 15 (51-104) | 17 |
| $^{111}$In-HH1 | 66 ± 14 (51-78) | 22 ± 12 (9-32) | 3 |
| $^{177}$Lu-HH1 | 56 | 92 | 1 |
| $^{125}$I-rituximab | 62 ± 6 (54-68) | 69 ± 30 (34-118) | 6 |
| $^{111}$In-rituximab | 45 | 16 | 1 |
| $^{177}$Lu-rituximab | 60 | 137 | 1 |

[1]Mean ± SD (range)

TABLE 2

The mean number of antigens ($B_{max}$) on Raji, Rael and Daudi cells, the equilibrium dissociation constant ($K_d$) and the association rate constant ($k_a$) for the antibodies rituximab and HH1.

| Antibody | Cell line | $B_{max}$(Ag/cell) | $K_d$ (nM) | $k_a$ (nM/h) |
|---|---|---|---|---|
| HH1 | Raji | 146 000 ± 7 600 | 6.3 ± 1.7 | 0.36 ± 0.14 |
| HH1 | Rael | 263 000 ± 27 000 | 12.7 ± 5.5 | 0.07 ± 0.01 |
| HH1 | Daudi | 340 000 ± 5 000 | 2.7 ± 0.3 | 0.72 ± 0.07 |
| rituximab | Raji | 272 000 ± 69 000 | 4.8 ± 0.9 | 0.08 ± 0.006 |
| rituximab | Rael | 626 000 ± 36 000 | 12.0 ± 2.0 | 0.08 ± 0.007 |

TABLE 3

Number of $^{177}$Lu atoms bound per Daudi cell after 2 hours of incubation.

| Antibody dosage | $^{177}$Lu-HH1 | | | $^{177}$Lu-rituximab | | |
|---|---|---|---|---|---|---|
| (μg/ml) | Unblocked | Blocked | Specific | Unblocked | Blocked | Specific |
| 0$^a$ | 12 | 7 | 5 | 8 | 53 | −45 |
| 1 | 8318 | 449 | 7869 | 8554 | 372 | 8182 |
| 2.5 | 9105 | 720 | 8385 | 11629 | 885 | 10744 |
| 5 | 10025 | 1837 | 8188 | 13658 | 2019 | 11639 |
| 10 | 13646 | 3521 | 10125 | 17344 | 2769 | 14575 |
| 20 | 16290 | 8473 | 7812 | 30095 | 9709 | 20386 |

($^a$The different counts for the control samples is indicative of the variation in background radiation to the counter).

TABLE 4

Number of $^{177}$Lu atoms bound per Daudi cell after 18 hours of incubation.

| Antibody dosage | $^{177}$Lu-HH1 | | | $^{177}$Lu-rituximab | | |
|---|---|---|---|---|---|---|
| (μg/ml) | Unblocked | Blocked | Net | Unblocked | Blocked | Net |
| 0 | 12 | 5 | 7 | 10 | 53 | −43 |
| 1 | 10327 | 301 | 10026 | 12831 | 356 | 12475 |
| 2.5 | 11757 | 787 | 10970 | 18836 | 1385 | 17451 |
| 5 | 12123 | 1857 | 10266 | 24097 | 1871 | 22226 |
| 10 | 11548 | 3205 | 8343 | 24249 | 2860 | 21389 |
| 20 | 15233 | 5445 | 9788 | 26639 | 5824 | 20815 |

TABLE 5

Binding fraction of four anti-CD37 antibodies.

| Antibody | IRF |
|---|---|
| HH1 | 50% |
| O.N.108 | 24% |
| IPO-24 | 16% |
| 6D263 | 21% |

REFERENCES

Bernstein I D, Eary J F, Badger C C, Press O W, Appelbaum F R, Martin P J, Krohn K A, Nelp W B, Porter B, Fisher D, Miller R, Brown S, Levy R, Donnall Thomas E. High dose radiolabelled antibody therapy of lymphoma. Cancer Res. 1990, 50(3 Suppl), 1017s-1021s.

Brechbiel M W. Bifunctional chelates for metal nuclides. Q J Nucl Med Mol Imaging 2008, 52 (2), 166-173.

Buchegger F, Antonescu C, Delaloye A B, Helg C, Kovacsovics T, Kosinski M, Mach J P, Ketterer N. Long-term complete responses after $^{131}$I-tositumomab therapy for relapsed or refractory indolent non-Hodgkin's lymphoma. Br J. Cancer. 2006, 94(12), 1770-6.

Dahle, J., Krogh, C., Melhus, K. B., Kaalhus, O., Larsen, R. H. and Stokke, T. A one-step method for determining the maximum number of bound antibodies, and the affinity and association rate constant of antibody binding. Nuclear Medicine Communications. 2007, 28, 742-747.

Gordon L I, Molina A, Witzig T, Emmanouilides C, Raubtischek A, Darif M, Schilder R J, Wiseman G, White C A. Durable responses after ibritumomab tiuxetan radioimmunotherapy for CD20+ B-cell lymphoma: long-term follow-up of a phase 1/2 study. Blood. 2004, 103(12), 4429-31.

Grosmaire L S, Hayden-Ledbetter M S, Ledbetter J A, Thompson P A, Simon S A, Brady W. B-cell reduction using CD37-specific and CD20-specific binding molecules. US 2007/0059306 A1

Heather A. Jacene, Ross Filice, Wayne Kasecamp, and Richard L. Wahl. Comparison of $^{90}$Y-Ibritumomab Tiuxetan and $^{131}$I-Tositumomab in Clinical Practice. J Nucl Med. 2007, 48, 1767-1776.

Heider K H, Borges E, Ostermann E. Anti CD37 antibodies. WO 2009/019312.

Henriksen G, Funderud S, Hoff P. Bi-labelled antibody and Bi-labelled streptavidin. Comparison of targeting efficacy of a lymphoma cell line in vitro. J Labelled Compds Radiopharm. 1997, 34(12), 1039-1046.

Hemminki A., Hoffrén A-M., Takkinen K., Vehniäinen M., Mäkinen M-L., Pettersson K., Teleman O., Söderlund H., Teeri T. T. Introduction of lysine residues on the light chain constant domain improves the labeling properties of a recombinant Fab fragment. Protein Engineering. Vol. 8, No. 2, pp. 185-191, 1995.

Liu S. Bifunctional coupling agents for radiolabeling of biomolecules and target-specific delivery of metallic radionuclides. Adv Drug Deliv Rev. 2008, 60 (12), 1347-1370.

Ngo N T, Brodie C, Giles C, Horncastle D, Klammer M, Lampert I A, Rahemtulla A, Naresh K N. The significance of tumour cell immunophenotype in myeloma and its impact on clinical outcome. J Clin Pathol. 2009, 62(11), 1009-15.

Press O W, Eary J F, Appelbaum F R, Martin P J, Badger C C, Nelp W B, Glenn S, Butchko G, Fisher D, Porter B, Matthews D C, Fisher L D, and Bernstein I D Radiolabeled-antibody therapy of B-cell lymphoma with autologous bone marrow support. N Engl J. Med. 1993, 329(17), 1219-24.

Press O W, Leonard J P, Coiffier B, Levy R, Timmerman J. Immunotherapy of Non-Hodgkin's lymphomas. Hematology Am Soc Hematol Educ Program. 2001, 221-40.

Smeland E, Funderud S, Ruud E, Kiil Blomhoff H, Godal T. Characterization of two murine monoclonal antibodies reactive with human B cells. Their use in a high-yield, high-purity method for isolation of B cells and utilization of such cells in an assay for B-cell stimulating factor. Scand J. Immunol. 1985, 21(3), 205-14.

What is claimed is:

1. A radioimmunoconjugate that binds human CD37 comprising:
   a) an anti-CD37 antibody comprising an immunoglobulin heavy chain and an immunoglobulin light chain, wherein the heavy chain comprises the amino acid sequence of SEQ ID NO: 2 and the light chain comprises the amino acid sequence of SEQ ID NO: 4,
   b) a chelating linker, and
   c) a radionuclide selected from the group consisting of $^{177}$Lu, $^{225}$Ac, $^{227}$Th, $^{212}$Pb, and $^{90}$Y.

2. The radioimmunoconjugate of claim 1, wherein said antibody is a monoclonal antibody.

3. A pharmaceutical composition comprising the radioimmunoconjugate according to claim 1, and a pharmaceutically acceptable carrier.

4. The pharmaceutical composition according to claim 3, further comprising one or more additional antibodies or radioimmunoconjugates.

5. The pharmaceutical composition according to claim 3, wherein the one or more additional antibodies or radioimmunoconjugates are specific for CD20.

6. A method of inhibiting a B-cell malignancy comprising: providing the radioimmunoconjugate according to claim 1 to a subject in need thereof, wherein said subject has non-Hodgkin lymphoma or chronic lymphocytic leukemia.

7. The method according to claim 6, wherein the radioimmunoconjugate is administered in combination with or in addition to another therapy.

8. The method according to claim 7, wherein the therapy is selected from the group consisting of chemotherapy, monoclonal antibody therapy, surgery, radiotherapy, and photodynamic therapy or a combination thereof.

9. The method according to claim 7, wherein the therapy comprises administration of an anti-CD20 and/or anti-CD37 monoclonal antibody prior to the treatment with the radioimmunoconjugate.

10. A kit for the production of the radioimmunoconjugate according to claim 1 comprising two or more vials, wherein one vial contains a conjugate comprising a chelator linked to an anti-CD37 antibody comprising an immunoglobulin heavy chain and an immunoglobulin light chain, wherein the heavy chain comprises the amino acid sequence of SEQ ID NO: 2 and the light chain comprises the amino acid sequence of SEQ ID NO: 4; and a second vial contains a radionuclide.

11. The kit according to claim 10, wherein the content of one or several of the vials are either lyophilized or in a solution.

\* \* \* \* \*

SEQUENCE LISTING

<160> NUMBER OF SEQ ID NOS: 4

<210> SEQ ID NO 1
<211> LENGTH: 357
<212> TYPE: DNA
<213> ORGANISM: Mus musculus

<400> SEQUENCE: 1

| | | |
|---|---|---|
| gagatccagc tgcagcagtc tggacctgag ctggtgaagc ctggggcttc agtgaaggta | 60 | |
| tcctgcaagg cttctggtta ctcattcact gactacaaca tgtactgggt gaagcagagc | 120 | |
| catggaaaga gccttgagtg gattggatat attgatcctt acaatggtga tactacctac | 180 | |
| aaccagaagt tcaagggcaa ggccacattg actgttgaca gtcctccag cacagccttc | 240 | |
| atccatctca acagcctgac atctgaggac tctgcagtct attactgtgc aagatcccct | 300 | |
| tatggtcact atgctatgga ctactgggt caaggaacct cagtcaccgt ctcctca | 357 | |

<210> SEQ ID NO 2
<211> LENGTH: 119
<212> TYPE: PRT
<213> ORGANISM: Mus musculus

<400> SEQUENCE: 2

Glu Ile Gln Leu Gln Gln Ser Gly Pro Glu Leu Val Lys Pro Gly Ala
1               5                   10                  15

Ser Val Lys Val Ser Cys Lys Ala Ser Gly Tyr Ser Phe Thr Asp Tyr
            20                  25                  30

Asn Met Tyr Trp Val Lys Gln Ser His Gly Lys Ser Leu Glu Trp Ile
        35                  40                  45

Gly Tyr Ile Asp Pro Tyr Asn Gly Asp Thr Thr Tyr Asn Gln Lys Phe
    50                  55                  60

Lys Gly Lys Ala Thr Leu Thr Val Asp Lys Ser Ser Thr Ala Phe
65                  70                  75                  80

Ile His Leu Asn Ser Leu Thr Ser Glu Asp Ser Ala Val Tyr Tyr Cys
                85                  90                  95

Ala Arg Ser Pro Tyr Gly His Tyr Ala Met Asp Tyr Trp Gly Gln Gly
            100                 105                 110

Thr Ser Val Thr Val Ser Ser
        115

<210> SEQ ID NO 3
<211> LENGTH: 321
<212> TYPE: DNA
<213> ORGANISM: Mus musculus

<400> SEQUENCE: 3

| | | |
|---|---|---|
| gacattgtga tgacccagtc tcacaaactc ttgtccacat cagtaggaga cagggtcagc | 60 | |
| atcacctgca aggccagtca ggatgtgagt actgctgtag actggtatca acagaaacca | 120 | |
| ggacaatctc ctaaactact gattaactgg gcatccaccc ggcacactgg agtccctgat | 180 | |
| cgcttcacag gcagtggatc tgggacagat tatactctca ccatcagcag tatgcaggct | 240 | |
| gaagacctgg cactttatta ctgtcgacaa cattatagca ctccattcac gttcggctcg | 300 | |
| gggacaaagt tggaaataaa a | 321 | |

<210> SEQ ID NO 4
<211> LENGTH: 107
<212> TYPE: PRT
<213> ORGANISM: Mus musculus

<400> SEQUENCE: 4

Asp Ile Val Met Thr Gln Ser His Lys Leu Leu Ser Thr Ser Val Gly
1               5                   10                  15

Asp Arg Val Ser Ile Thr Cys Lys Ala Ser Gln Asp Val Ser Thr Ala
            20                  25                  30

Val Asp Trp Tyr Gln Gln Lys Pro Gly Gln Ser Pro Lys Leu Leu Ile

-continued

```
            35                  40                  45
Asn Trp Ala Ser Thr Arg His Thr Gly Val Pro Asp Arg Phe Thr Gly
        50                  55                  60

Ser Gly Ser Gly Thr Asp Tyr Thr Leu Thr Ile Ser Ser Met Gln Ala
65                  70                  75                  80

Glu Asp Leu Ala Leu Tyr Tyr Cys Arg Gln His Tyr Ser Thr Pro Phe
                85                  90                  95

Thr Phe Gly Ser Gly Thr Lys Leu Glu Ile Lys
            100                 105
```